United States Patent
Yakushiji

(10) Patent No.: US 11,733,759 B2
(45) Date of Patent: Aug. 22, 2023

(54) POWER SUPPLY CONTROL CIRCUIT AND DRUG SOLUTION ADMINISTRATION APPARATUS INCLUDING THE POWER SUPPLY CONTROL CIRCUIT

(71) Applicant: TERUMO KABUSHIKI KAISHA, Tokyo (JP)

(72) Inventor: Yusuke Yakushiji, Kanagawa (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 58 days.

(21) Appl. No.: 17/487,521

(22) Filed: Sep. 28, 2021

(65) Prior Publication Data

US 2022/0011845 A1   Jan. 13, 2022

Related U.S. Application Data

(63) Continuation of application No. PCT/JP2020/007771, filed on Feb. 26, 2020.

(30) Foreign Application Priority Data

Mar. 28, 2019 (JP) ................. 2019-064560

(51) Int. Cl.
*G06F 1/3228* (2019.01)
*G06F 1/3287* (2019.01)
*G06F 1/329* (2019.01)

(52) U.S. Cl.
CPC ............ *G06F 1/3228* (2013.01); *G06F 1/329* (2013.01); *G06F 1/3287* (2013.01)

(58) Field of Classification Search
CPC ...... G06F 1/3228; G06F 1/3287; G06F 1/329; G06F 1/32

(Continued)

(56) References Cited

U.S. PATENT DOCUMENTS 6,388,343 B1 * 5/2002 Michigami ............... G06F 1/26
                                                         307/112
2009/0153236 A1   6/2009 Kneepkens et al.
(Continued)

FOREIGN PATENT DOCUMENTS

JP      05265599    * 10/1993
JP      H05265599 A   10/1993
(Continued)

OTHER PUBLICATIONS

The extended European Search Report dated Mar. 16, 2022, by the European Patent Office in corresponding European Patent Application No. 20778434.9-1216. (13 pages).

(Continued)

*Primary Examiner* — Chun Cao
(74) *Attorney, Agent, or Firm* — Buchanan Ingersoll & Rooney PC

(57) ABSTRACT

A power supply control circuit capable of achieving power saving. The power supply control circuit includes: a microcomputer that controls an operation of a control target; a power supply unit that supplies power to the microcomputer; a power switch that connects the power supply unit and the microcomputer; a bypass circuit that includes a MOSFET switch and is capable of bypassing the power switch to maintain connection between the power supply unit and the microcomputer; and a cut-off circuit that includes a MOSFET switch and is disposed between the bypass circuit and the microcomputer.

16 Claims, 7 Drawing Sheets

(58) Field of Classification Search
USPC .................................................. 713/300, 320
See application file for complete search history.

(56) References Cited

U.S. PATENT DOCUMENTS

| | | | | |
|---|---|---|---|---|
| 2013/0187471 A1* | 7/2013 | Kim | ...................... | H02J 7/0068 |
| | | | | 307/66 |
| 2015/0188348 A1* | 7/2015 | Yokota | .................. | H02J 7/0063 |
| | | | | 320/135 |

FOREIGN PATENT DOCUMENTS

| | | |
|---|---|---|
| JP | H10240392 A | 9/1998 |
| JP | 2015128336 A | 7/2015 |
| JP | 2015181869 A | 10/2015 |

OTHER PUBLICATIONS

International Search Report (PCT/ISA/210) with translation and Written Opinion (PCT/ISA/237) dated Mar. 31, 2020, by the Japan Patent Office as the International Searching Authority for International Application No. PCT/JP2020/007771. (9 pages).

* cited by examiner

PRIOR ART

POWER SUPPLY CONTROL CIRCUIT AND DRUG SOLUTION ADMINISTRATION APPARATUS INCLUDING THE POWER SUPPLY CONTROL CIRCUIT

CROSS-REFERENCES TO RELATED APPLICATIONS

This application is a continuation of International Application No. PCT/JP2020/007771 filed on Feb. 26, 2020, which claims priority to Japanese Patent Application No. 2019-064560 filed on Mar. 28, 2019, the entire content of which is incorporated herein by reference.

FIELD OF THE DISCLOSURE

The present disclosure generally relates to a power supply control circuit capable of achieving power saving and a drug solution administration apparatus including the power supply control circuit.

BACKGROUND DISCUSSION

Japanese Patent Application Publication No. 2015-181869 A discloses a syringe pump type drug solution administration apparatuses for administering a drug solution filled in a drug solution container to a living body. A syringe pump type drug solution administration apparatus includes a power source, a microcomputer, and a drive device, and is capable of continuously administering a drug solution with high precision over a relatively long period of time with the drive device causing a pusher to move little by little.

This type of drug solution administration apparatus may be stored under refrigeration without being powered on for a relatively long time on the order of years (for example, for several years) after manufactured in a factory until used in a hospital or the like. When the power switch of the drug solution administration apparatus is turned on immediately before use, an electrical closed circuit including a battery is formed so that a drug solution can be administered.

The size of a drug solution administration apparatus is minimized for purposes including achieving easier handling when the apparatus is in use and storage-space saving when the apparatus is stored. For this reason, a small-sized button battery (i.e., a coin battery) can be employed as the power source. In addition, the microcomputer is provided with a protection circuit so that the microcomputer is not damaged by noise.

During the storage under refrigeration, the main power is not supplied to the microcomputer in the drug solution administration apparatus because the power switch is not turned on, although a button battery stays inserted in the apparatus. However, during the storage under refrigeration, a leakage current flows through the protection circuit to consume the power of the button battery. In a case where the drug solution administration apparatus is stored under refrigeration for a relatively long time, the leakage current reduces the capacity of the button battery, with the result that the drug solution administration apparatus in actual use may fail to administer the full amount of the drug solution to the user because of the insufficient capacity. A solution to avoiding such situation is to increase the capacity of the button battery in anticipation of the consumption caused by the leakage current, but such solution cannot be selected because the solution hinders reduction in size and cost of the drug solution administration apparatus.

SUMMARY

A power supply control circuit is disclosed capable of achieving power saving and a drug solution administration apparatus including the power supply control circuit.

A power supply control circuit is disclosed, which includes: a controller that controls an operation of a control target; a power supply unit that supplies power to the controller; a power switch that connects the power supply unit and the controller; a bypass circuit that includes a first semiconductor switch and is capable of bypassing the power switch to maintain connection between the power supply unit and the controller; and a cut-off circuit that includes a second semiconductor switch and is disposed between the bypass circuit and the controller, in which when the second semiconductor switch is in an off state, a leakage current generated between the controller and the power supply unit via the bypass circuit is cut off by the cut-off circuit, and when the second semiconductor switch is turned on by a switch-on signal output from the controller, the first semiconductor switch is turned on and the bypass circuit bypasses the power switch to maintain connection between the power supply unit and the controller.

A drug solution administration apparatus is disclosed, which includes a power supply control circuit that includes: a controller that controls an operation of a control target; a power supply unit that supplies power to the controller; a power switch that connects the power supply unit and the controller; a bypass circuit that includes a first semiconductor switch and is capable of bypassing the power switch to maintain connection between the power supply unit and the controller; and a cut-off circuit that includes a second semiconductor switch and is disposed between the bypass circuit and the controller, in which when the second semiconductor switch is in an off state, a leakage current generated between the controller and the power supply unit via the bypass circuit is cut off by the cut-off circuit, and when the second semiconductor switch is turned on by a switch-on signal output from the controller, the first semiconductor switch is turned on and the bypass circuit bypasses the power switch to maintain connection between the power supply unit and the controller.

In accordance with an aspect, a drug solution administration system is disclosed comprising: a drug solution administration apparatus, the drug solution administration apparatus comprising: a drug solution container configured to hold a drug solution; a housing that holds the drug solution container; a pusher configured to push the drug solution contained in the drug solution container; a drive mechanism configured to move forward the pusher toward a distal end of the drug solution container; a detection part configured to sense a to-be-detected part of the pusher to detect completion of delivery of the drug solution on the basis of a sensing result; a controller configured to control operations of the drive mechanism to be controlled, the controller comprising: a power supply unit configured to supply power to the controller; a power switch configured to connect the power supply unit and the controller; a bypass circuit that includes a first semiconductor switch and is capable of bypassing the power switch to maintain connection between the power supply unit and the controller; a cut-off circuit that includes a second semiconductor switch and is disposed between the bypass circuit and the controller; wherein when the second semiconductor switch is in an off state, a leakage current generated between the controller and the power supply unit via the bypass circuit is cut off by the cut-off circuit; and when the second semiconductor switch is turned on by a switch-on signal output from the controller, the first semiconductor switch is turned on and the bypass circuit bypasses the power switch to maintain connection between the power supply unit and the controller.

In accordance with another aspect, a method is disclosed of controlling power supply to a drug solution administration apparatus with a controller configured to control an operation of a control target, the method comprising: supplying power to the controller from a power supply unit; connecting the power supply unit and the controller with a power switch; bypassing the power switch to maintain connection between the power supply unit and the controller with a bypass circuit that includes a first semiconductor switch; disposing a cut-off circuit that includes a second semiconductor switch between the bypass circuit and the controller; wherein when the second semiconductor switch is in an off state, generating a leakage current between the controller and the power supply unit via the bypass circuit is cut off by the cut-off circuit; and when the second semiconductor switch is turned on by a switch-on signal output from the controller, turning on the first semiconductor switch and bypassing the power switch with the bypass circuit to maintain connection between the power supply unit and the controller.

The power supply control circuit and the drug solution administration apparatus including the power supply control circuit according to the present disclosure can achieve power saving during storage before the apparatus is powered on because the leakage circuit can be cut off. In addition, reduction in size and cost of the drug solution administration apparatus can be achieved.

DETAILED DESCRIPTION

Figure 1:
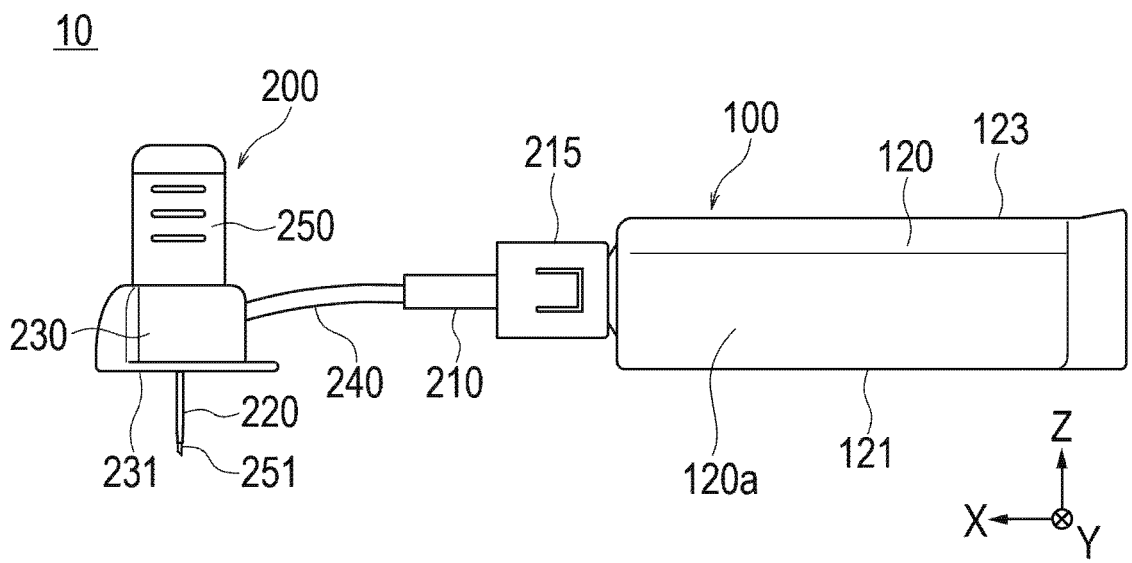
FIG. 1 is a side view of a drug solution administration system.

Set forth below with reference to the accompanying drawings is a detailed description of embodiments of a power supply control circuit capable of achieving power saving and a drug solution administration apparatus including the power supply control circuit. Note that since embodiments described below are preferred specific examples of the present disclosure, although various technically preferable limitations are given, the scope of the present disclosure is not limited to the embodiments unless otherwise specified in the following descriptions. In addition, dimensional ratios in the drawings are exaggerated for convenience of description and may be different from actual ratios.

Figure 2:
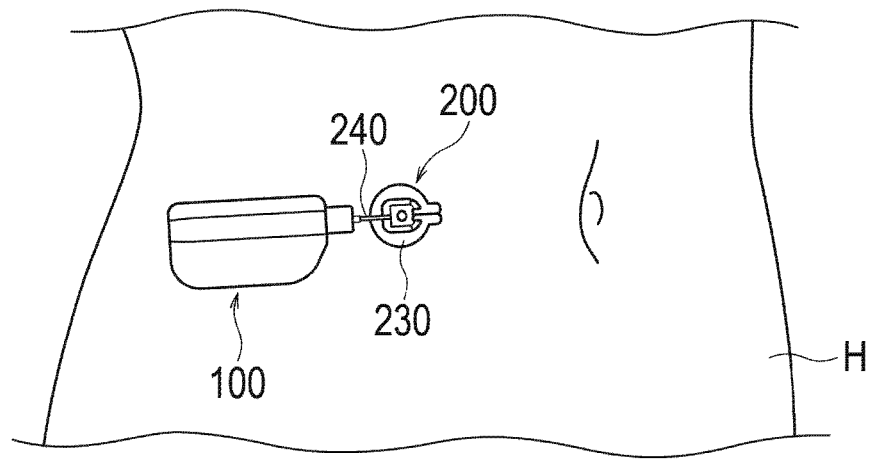
FIG. 2 is a diagram schematically illustrating a usage example of the drug solution administration system.
Figure 3:
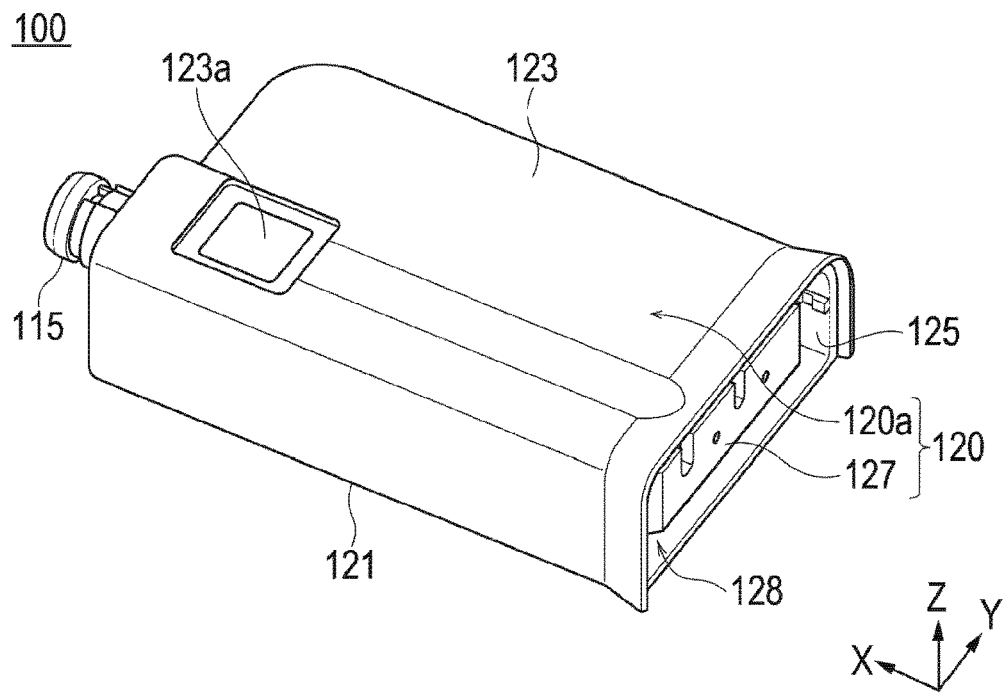
FIG. 3 is a schematic perspective view of the drug solution administration apparatus.
Figure 4:
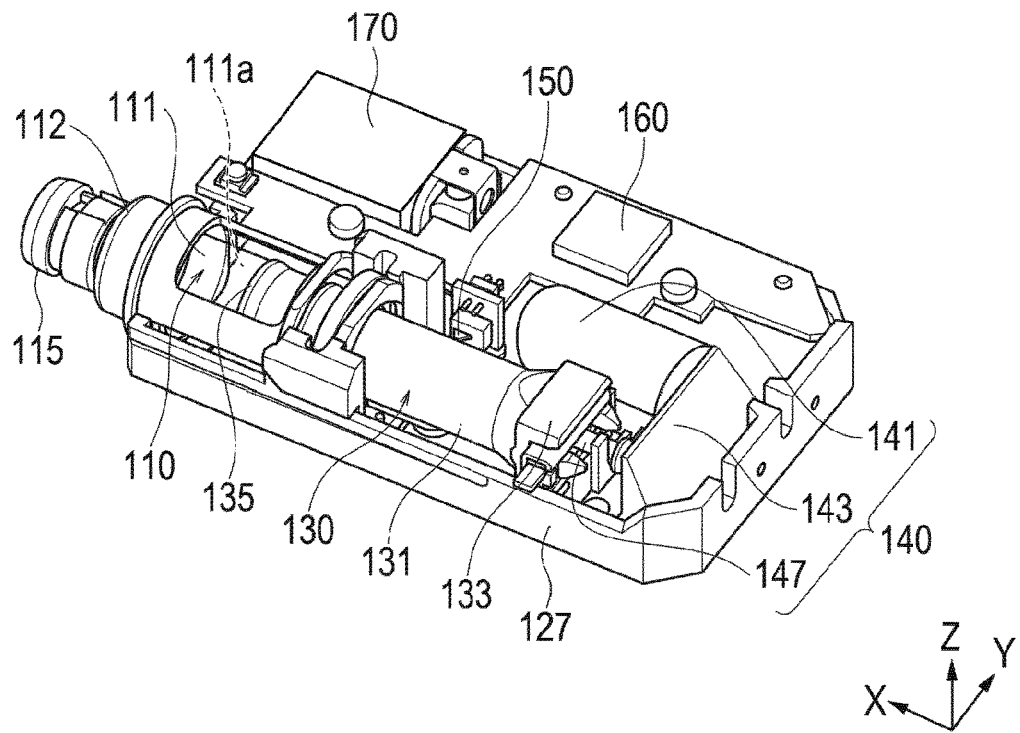
FIG. 4 is a schematic perspective view of a chassis included in a housing and of individual components assembled to the chassis.
Figure 5:
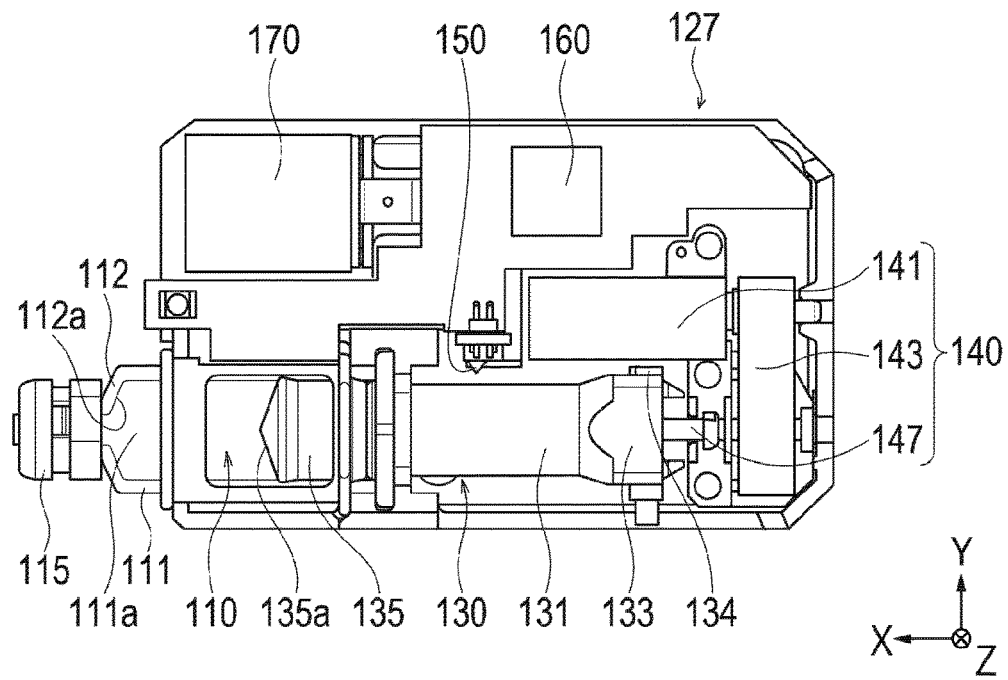
FIG. 5 is a plan view of the drug solution administration apparatus in a state where a pusher is not moved forward yet.
Figure 6:
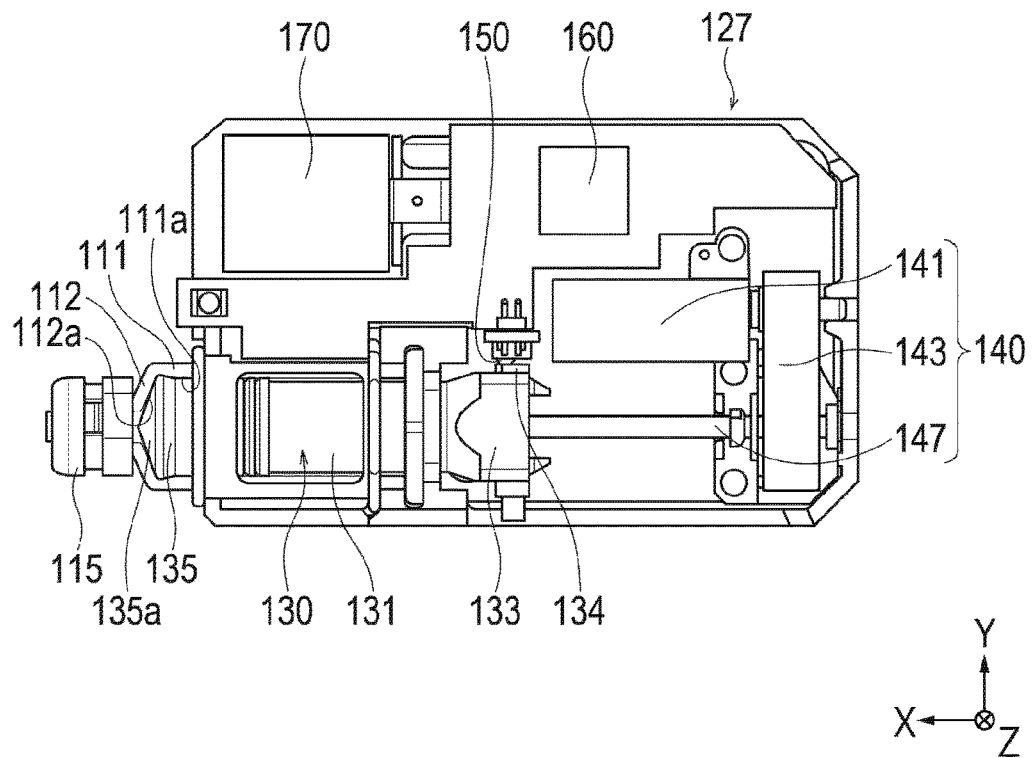
FIG. 6 is a plan view of the drug solution administration apparatus in a state where the pusher has been moved forward.

FIGS. 1 to 6 are diagrams for explaining a drug solution administration system 10, a drug solution administration apparatus 100, and an administration instrument 200 according to the present embodiment. FIG. 1 is a side view of the drug solution administration system. FIG. 2 is a diagram schematically illustrating a usage example of the drug solution administration system. FIG. 3 is a schematic perspective view of the drug solution administration apparatus. FIG. 4 is a schematic perspective view of a chassis included in a housing and of individual components assembled to the chassis. FIG. 5 is a plan view of the drug solution administration apparatus in a state where a pusher is not moved forward yet. FIG. 6 is a plan view of the drug solution administration apparatus in a state where the pusher has been moved forward. In the drawings, an arrow X indicates the "longitudinal direction (longitudinal direction of a drug solution container 110)" of the drug solution administration apparatus 100, an arrow Y indicates the "width direction (depth direction)" of the drug solution administration apparatus 100, and an arrow Z indicates the "height direction" of the drug solution administration apparatus 100.

Drug Solution Administration System

The drug solution administration system 10 can be used for administering a drug solution into a living body. As illustrated in FIG. 1, the drug solution administration system 10 includes a drug solution administration apparatus 100 and an administration instrument 200.

As illustrated in FIG. 2, the drug solution administration apparatus 100 and the administration instrument 200 are configured as patch-type devices to be attached to a body surface (skin) H of the user before use. The site of the user body to which the drug solution administration apparatus 100 and the administration instrument 200 are attached is not particularly limited, and examples of the site of the user body can include the abdomen and thighs.

In accordance with an exemplary embodiment, the drug solution administration system 10 is capable of continuously administering a drug solution filled in a drug solution container 110 included in the drug solution administration apparatus 100 into a living body over a relatively long period of time (for example, about several minutes to several hours) by a pressing action provided by a pusher 130 (see FIG. 4). Note that the drug solution administration system 10 may intermittently administer a drug solution into a living body.

Drug Solution Administration Apparatus

As illustrated in FIGS. 3 to 6, the drug solution administration apparatus 100 includes: the drug solution container 110 that includes a body 111 being tubular (barrel-shaped) and filled with a drug solution; a housing 120 that holds the drug solution container 110; the pusher 130 that pushes out the drug solution contained in the drug solution container 110; a drive mechanism 140 that moves forward the pusher 130 toward the distal end opening of the drug solution container 110; a detection part 150 that senses a to-be-detected part 134 of the pusher 130 to detect completion of delivery of the drug solution on the basis of a sensing result; and a control unit 160 that controls operations of the drive mechanism to be controlled.

As illustrated in FIGS. 3 and 4, the housing 120 includes: a housing body 120a that is box-shaped and has an accommodation space 128 formed in the housing body 120; and a chassis (corresponding to a "support part") 127 that is housed in the accommodation space 128 of the housing body 120*a* and can be fixed to the housing body 120*a*.

As illustrated in FIG. 3, a window part 123*a* is formed on a top surface 123 of the housing body 120*a* so that the inside of the accommodation space 128 can be visually recognized from the outside of the housing 120. The window part 123*a* is formed by providing a transparent or translucent portion in a part of the housing body 120*a*.

A proximal end opening 125 for inserting the chassis 127 into the accommodation space 128 of the housing body 120*a* is formed on the proximal end side of the housing body 120*a* with respect to its longitudinal direction. The proximal end opening 125 of the housing body 120*a* is covered by a lid member (not illustrated) in a state where the chassis 127 is housed in the accommodation space 128.

On a bottom surface 121 of the housing body 120*a*, a sheet-like sticking part that can be stuck on the body surface H of the user is provided. In an initial state before the drug solution administration apparatus 100 is attached to the user, a peelable protective sheet is attached to the sticking surface of the sticking part.

As illustrated in FIG. 4, the drug solution container 110, the pusher 130, the drive mechanism 140, the detection part 150, the control unit 160, and the power supply unit 170 are held in the chassis 127.

The drug solution container 110 can be formed, for example, of a so-called prefilled type drug solution container. Therefore, the drug solution is filled in advance in an inner cavity 111*a* of the body 111 of the drug solution container 110. Examples of the drug solution can include protein preparations, narcotic analgesics, and diuretics.

A sealing member for preventing leakage of the drug solution can be disposed at the distal end opening (discharge port) formed at a distal end 112 of the drug solution container 110. As illustrated in FIG. 3, the distal end opening of the drug solution container 110 is disposed so as to protrude outward from the housing body 120*a*. On the drug solution container 110, an attachment 115 to be connected to a tube 240 (see FIG. 1) can be attached to the distal end protruding from the housing body 120*a*.

A body 131 of the pusher 130 is to be inserted into the inner cavity 111*a* of the body 111 of the drug solution container 110 (see FIGS. 4 and 5). A gasket 135 slidable on an inner wall of the drug solution container 110 is disposed at the distal end of the body 131 of the pusher 130. The gasket 135 liquid-tightly seals the proximal end side of the gasket 135 by bringing the outer periphery of the gasket 135 into close contact with the inner peripheral surface of the body 111 of the drug solution container 110 in a liquid-tight manner.

In the present embodiment, the gasket 135 is configured to be contractible in a direction (longitudinal direction) in which the pusher 130 moves forward when the pusher 130 moves forward in a state where the gasket 135 is pressed against a distal end inner wall 112*a* of the drug solution container 110 (see FIG. 5). The gasket 135 can be made of, for example, a rubber material or a flexible resin material such as an elastomer so as to be contractible as described above.

In accordance with an exemplary embodiment, as illustrated in FIG. 5, the gasket 135 has a tapered shape in which the outer diameter gradually decreases toward the distal end side. In addition, the gasket 135 is formed to have substantially the same shape as the shape of the distal end inner wall 112*a* of the drug solution container 110.

As illustrated in FIG. 5, the to-be-detected part 134 is provided at the proximal end of the pusher 130. The to-be-detected part 134 can be used for detecting completion of delivery of a drug solution by the drug solution administration apparatus 100.

The control unit 160 controls drug solution delivery operations of the drug solution administration apparatus 100. The control unit 160 can be formed of, for example, a microcomputer (electronic circuit element) in which a central processing unit (CPU), a random-access memory (RAM), a read-only memory (ROM), and the like are mounted. The control unit 160 controls operations of the drive mechanism 140, the detection part 150, the power supply unit 170, and a notification unit in a centralized manner (i.e., the drive mechanism 140, the detection part 150, the power supply unit 170, and the notification unit comprises one or more control targets). The control unit 160 further includes a power supply control circuit for minimizing power consumption in the power supply unit 170 during the period of time from manufacture of the drug solution administration apparatus 100 to use of the drug solution administration apparatus 100 by the user. The power supply control circuit will be described later in detail.

As illustrated in FIG. 5, the detection part 150 is disposed in the chassis 127. As illustrated in FIG. 6, the detection part 150 detects completion of drug delivery by the drug solution administration apparatus 100 when the to-be-detected part 134 included in the pusher 130 comes into contact with the detection part 150. The detection part 150 can be formed of, for example, a known contact-type sensor that transmits a predetermined electric signal when the sensor comes into contact with the to-be-detected part 134. The control unit 160 obtains information about completion of drug delivery by receiving an electric signal from the detection part 150. Note that the detection part 150 is not particularly limited to any specific configuration as long as the position of the to-be-detected part 134 of the pusher 130 can be detected when the pusher 130 moves forward by a predetermined amount.

The power supply unit 170 can be formed of, for example, a button battery (i.e., coin battery), a power supply stabilizing circuit, and the like. The drug solution administration apparatus 100 is required to be smaller in size. Therefore, a particularly small power source is used as the power source of the power supply unit 170.

As illustrated in FIG. 4, the drive mechanism 140 can include a motor 141 that receives a drive current from the power supply unit 170 to generate a rotational driving force, a deceleration mechanism 143 including gears or the like for transmitting the rotational driving force of the motor 141, and a feed screw 147 connected to the deceleration mechanism 143.

The feed screw 147 is connected to a proximal end connection part 133 disposed near the proximal end of the pusher 130. The feed screw 147 converts a rotary motion transmitted from the deceleration mechanism 143 into a linear motion to move forward the pusher 130 in the longitudinal direction (X direction). The pusher 130 moves forward toward the distal end side of the drug solution container 110, thereby pushing the drug solution from the inner cavity 111*a* of the body 111 of the drug solution container 110 to the tube 240 (see FIG. 1).

Administration Instrument

As illustrated in FIGS. 1 and 2, the administration instrument 200 is configured to be connectable to the drug solution administration apparatus 100.

The administration instrument 200 includes a connector 210, a needle tube 220 for puncturing the living body, a puncture unit (cannula housing) 230, a tube 240, and a puncture aid 250 for assisting in puncturing the living body with the needle tube 220.

The connector 210 is configured to be connectable to the drug solution administration apparatus 100 via an attachment 215 that is fixed to the connector 210. The attachment 215 can be connected to the drug solution administration apparatus 100 by being fitted onto the attachment 115 (see FIG. 4) that is provided near the distal end 112 of the drug solution container 110 protruding outside from the housing 120.

Inside the attachment 215, a needle part for connection capable of punctuating a sealing member disposed at the distal end of the drug solution container 110 is disposed. The tube 240 communicates with the inner cavity 111a of the body 111 of the drug solution container 110 via the needle part for connection.

Inside the puncture unit 230, a flow path allowing the tube 240 and the inner cavity of the needle tube 220 to communicate with each other is formed. The drug solution delivered to the puncture unit 230 via the tube 240 passes through the flow path formed inside the puncture unit 230 and the needle tube 220 and is administered into the living body.

When the drug solution is going to be delivered to the user, the puncture aid 250 is attached to the puncture unit 230. The puncture aid 250 holds an introducer needle (inner needle) 251. In a state where the puncture aid 250 is attached to the puncture unit 230, the introducer needle 251 protrudes from the tip of the needle tube 220. By puncturing the living body with the needle tube 220 in a state where the introducer needle 251 is inserted through the needle tube 220, the user can insert the needle tube 220 into the living body while preventing breakage or the like of the needle tube 220.

After the living body is punctured with the needle tube 220, the puncture aid 250 is removed from the puncture unit 230. When the puncture aid 250 is removed from the puncture unit 230, the introducer needle 251 is removed from the inner cavity of the needle tube 220.

After the living body is punctured with the needle tube 220 and the puncture aid 250 is removed, the puncture unit 230 is left on the body surface H of the user with the needle tube 220 indwelling in the living body. In this state, the pusher 130 in the drug solution administration apparatus 100 moves forward inside the drug solution container 110, whereby the drug solution filled in the drug solution container 110 is delivered to the inner cavity of the needle tube 220 via the tube 240 and the flow path in the puncture unit 230.

The introducer needle 251 can be formed of, for example, a metal needle. The needle tube 220 can be formed of, for example, a tubular member (cannula) made of resin.

As with the drug solution administration apparatus 100, the administration instrument 200 is configured as a patch-type instrument to be attached to the body surface H of the user before use. A contact surface (bottom surface) 231 of the puncture unit 230 of the administration instrument 200 is provided with a sheet-like sticking part that can be stuck on the body surface H. In an initial state before the administration instrument 200 is attached to the user, a peelable protective sheet is attached to the sticking surface of the sticking part.

Schematic configurations of the drug solution administration system 10, the drug solution administration apparatus 100, and the administration instrument 200 have been described above. The drug solution administration apparatus 100 can be stored under refrigeration after manufactured in a factory until used by a user. During the storage under refrigeration, main power is not supplied from the power supply unit 170 to the control unit 160. However, for example, in a case where there is a bypass circuit that includes a MOSFET switch 162 and bypasses the power switch 161 as in a conventional power supply control circuit illustrated in FIG. 11, a leakage circuit can be formed via the bypass circuit between the microcomputer 164 and the power supply unit 170 separately from the main path. As a result, although the power switch 161 is off, power is continuously consumed during storage under refrigeration. Meanwhile, since the power source of the power supply unit 170 is formed, for example, of a button battery, power is continuously supplied from the power supply unit 170 to the control unit 160. The power supply unit 170 can be formed of a button battery (i.e., coin battery), and thus it is necessary to minimize the power consumed by the control unit 160 during storage under refrigeration. For this reason, the control unit 160 includes a power supply control circuit as described below.

Figure 7:
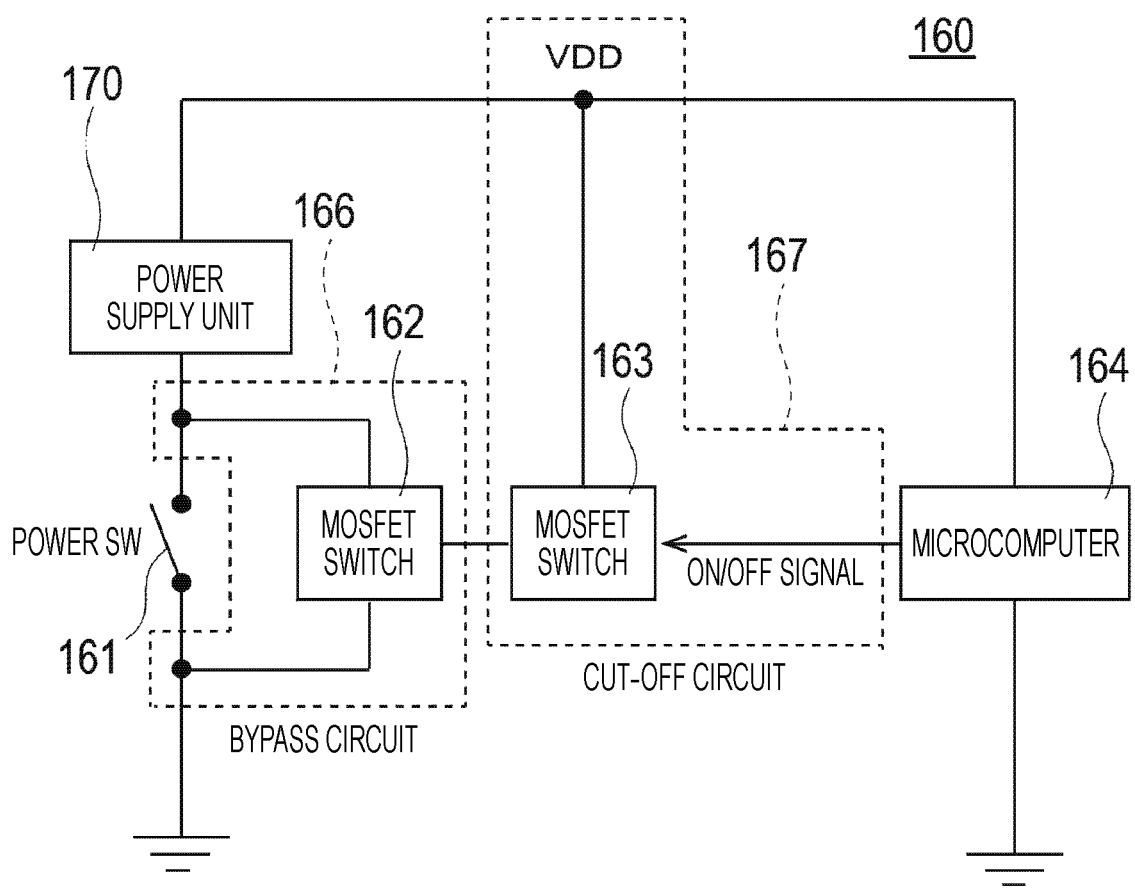
FIG. 7 is a block diagram of a power supply control circuit included in a control unit.
Figure 8:
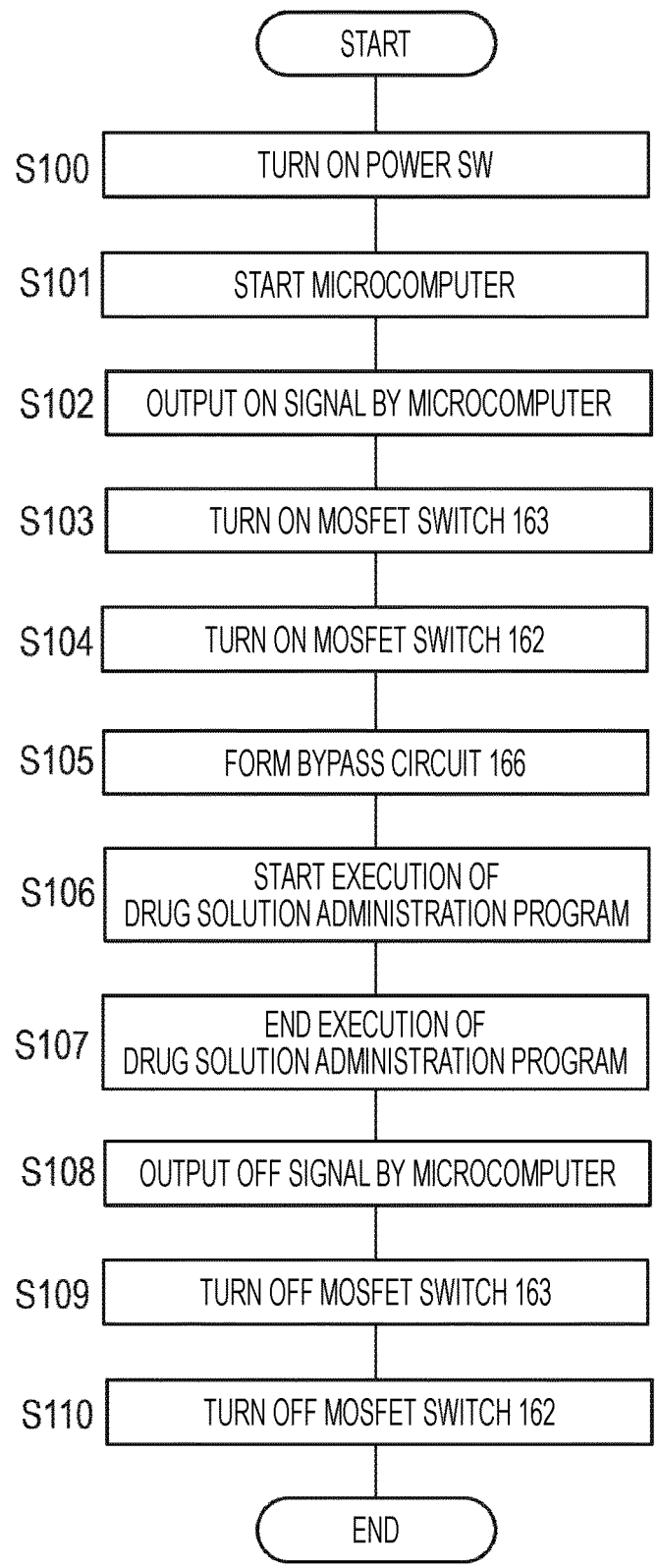
FIG. 8 is an operation flowchart for the drug solution administration apparatus.
Figure 9:
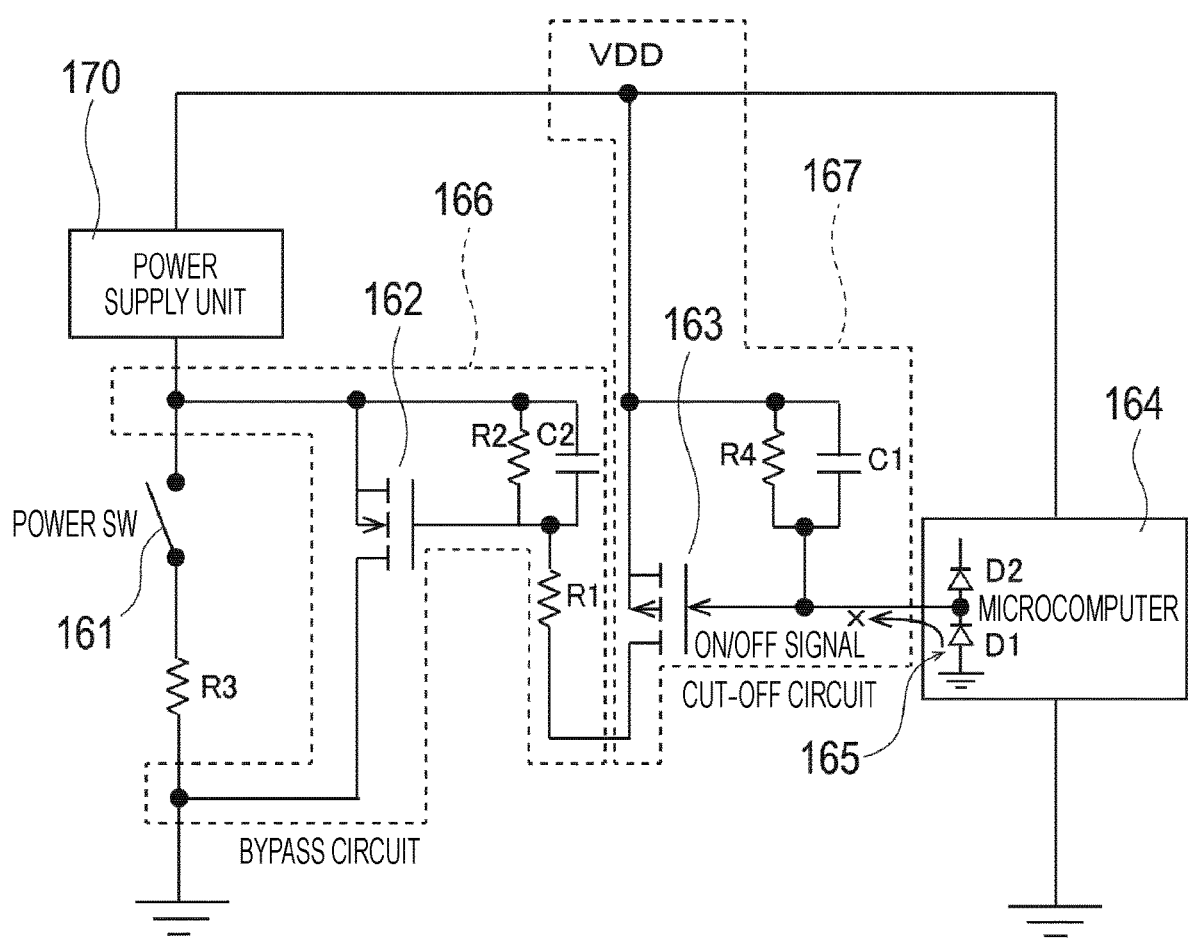
FIG. 9 is a diagram for explaining operations of the power supply control circuit.
Figure 10:
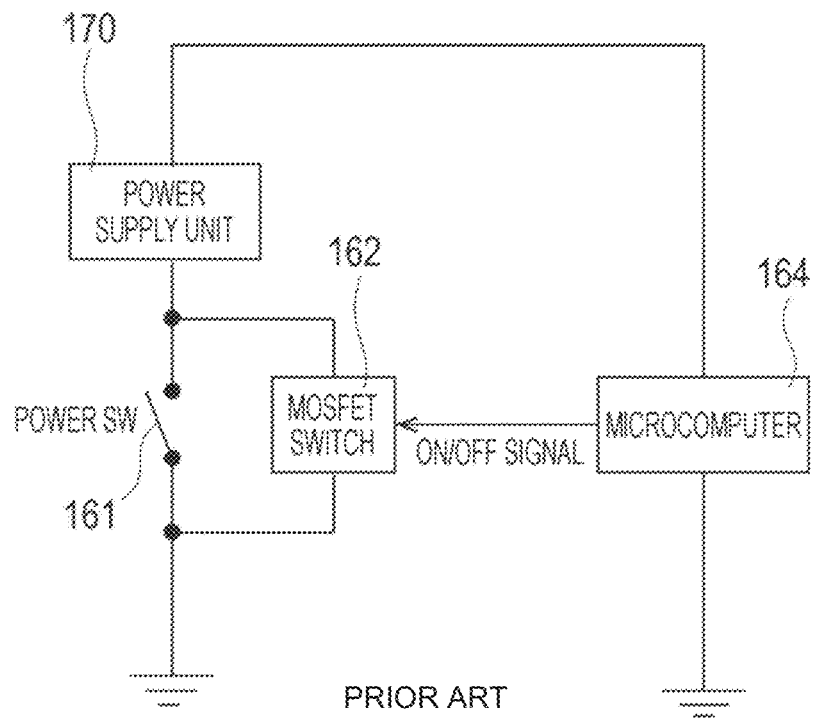
FIG. 10 is a block diagram of a power supply control circuit included in a conventional control unit.
Figure 11:
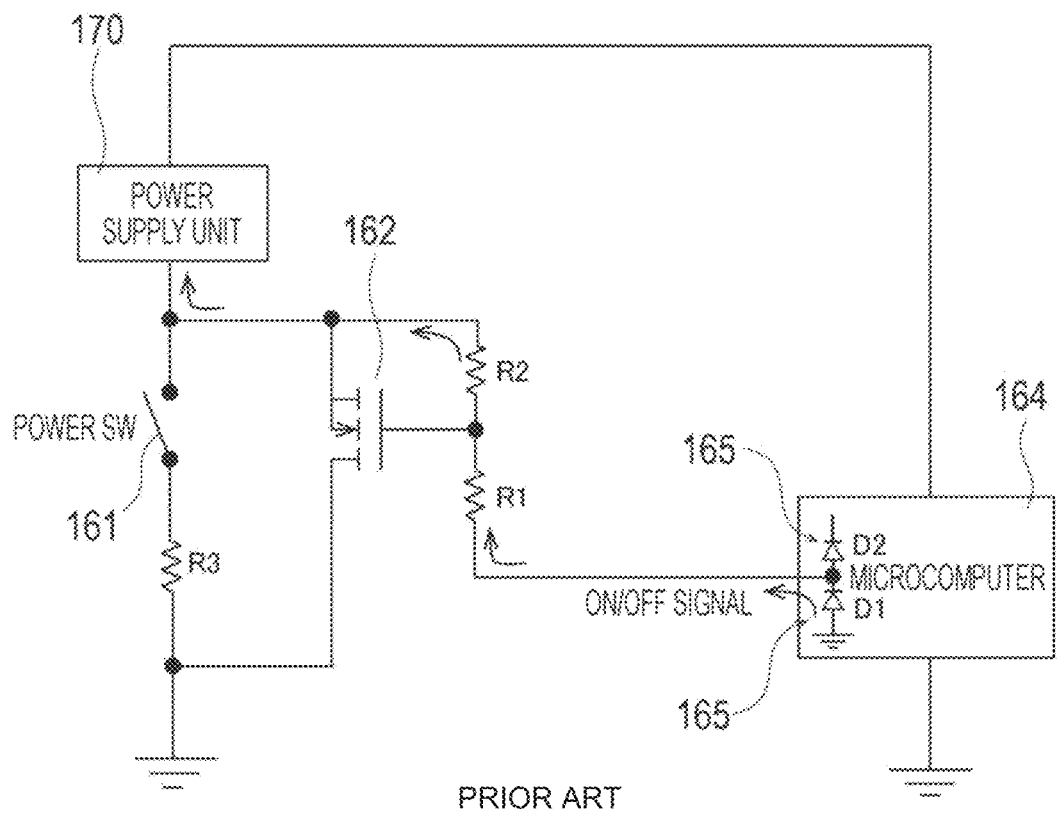
FIG. 11 is a diagram for explaining operations of a conventional power supply control circuit.

Specific configurations and operations of the power supply control circuit included in the control unit 160 will now be described with reference to FIGS. 7 to 11. FIG. 7 is a block diagram of the power supply control circuit included in the control unit. FIG. 8 is an operation flowchart for the drug solution administration apparatus. FIG. 9 is a diagram for explaining operations of the power supply control circuit. FIG. 10 is a block diagram of a power supply control circuit included in a conventional control unit. FIG. 11 is a diagram for explaining operations of a conventional power supply control circuit.

Configuration of Power Supply Control Circuit

In accordance with an exemplary embodiment, the power supply control circuit included in the control unit 160 can include a power switch (power SW) 161, a MOSFET switch 162 for forming a bypass circuit 166, a MOSFET switch 163 for forming a cut-off circuit 167, and a microcomputer 164 functioning as a controller.

The power switch 161 electrically connects the power supply unit 170 that supplies power to the microcomputer 164 and the microcomputer 164. Note that the power switch 161 can be, for example, a momentary operation type push-button switch that is on only when being pressed.

The MOSFET switch 162, which is a first semiconductor switch, is turned on by an ON signal output from the MOSFET switch 163 to bypass the power switch 161. After the power switch 161 is turned on, the MOSFET switch 162 bypasses the power switch 161 to keep the on state of the power switch 161. The MOSFET switch 162 forms a bypass circuit 166 capable of maintaining the connection between the power supply unit 170 and the microcomputer 164, bypassing the power switch 161.

The MOSFET switch 163, which is a second semiconductor switch, is turned on by an ON signal output from the microcomputer 164 when the power switch 161 is turned on, and outputs an ON signal to the MOSFET switch 162. The MOSFET switch 163 helps prevents the microcomputer 164 and the MOSFET switch 162 from being directly electrically connected to each other, and therefore the MOSFET switch 163 cuts off a leakage current flowing between the microcomputer 164 and the power supply unit 170 before power is applied. That is, the MOSFET switch 163 forms the cut-off circuit 167 disposed between the bypass circuit 166 and the microcomputer 164.

Therefore, when the MOSFET switch 163 is in the off state, a leakage current generated between the microcomputer 164 and the power supply unit 170 via the bypass circuit 166 is cut off by the cut-off circuit 167, and when the MOSFET switch 163 is turned on by a switch-on signal output from the microcomputer 164, the MOSFET switch 162 is turned on and the bypass circuit 166 bypasses the power switch 161 and maintains the connection between the power supply unit 170 and the microcomputer 164.

The MOSFET switch 163 supplies a bypass circuit ON signal for turning on the MOSFET switch 162 to the MOSFET switch 162. Therefore, the MOSFET switch 162 is turned on by the bypass circuit ON signal. The cut-off circuit 167 can include a signal supply source that supplies a bypass circuit ON signal for turning on the MOSFET switch 162.

In accordance with an exemplary embodiment, the bypass circuit 166 can include an upstream circuit branched from the upstream side of the power switch 161 and connected to the upstream side of the MOSFET switch 162, a downstream circuit connected from the downstream side of the MOSFET switch 162 to a circuit between the power switch 161 and the power supply unit 170, and a first input circuit for inputting a bypass circuit ON signal to the MOSFET switch 162 connected to the downstream side of the MOSFET switch 163 in the cut-off circuit 167. The first input circuit includes resistors R1 and R2, a capacitor C2, and the like in FIG. 9. In accordance with an exemplary embodiment, the capacitor C2 may be omitted.

The cut-off circuit 167 can include a signal supply source connected to the upstream side of the MOSFET switch 163, a second input circuit for inputting a switch-on signal from the microcomputer 164 to the MOSFET switch 163, and a branch circuit branched from the second input circuit and connected to a circuit between the signal supply source and the MOSFET switch 163. The second input circuit can include a resistor R4, a capacitor C1, and the like in FIG. 9. In accordance with an exemplary embodiment, the capacitor C1 may be omitted.

The signal supply source is a voltage supply circuit that supplies a voltage for turning on the MOSFET switch 162, and the voltage supply circuit is a circuit branched from a circuit between the downstream side of the power supply unit 170 and the microcomputer 164 for applying a power supply voltage VDD.

The microcomputer 164, which can be a microcomputer provided with a program for controlling operations of the above-described drive mechanism 140 and the like to be controlled, controls operations of the drive mechanism 140 and the like by executing the program.

As examples of the first semiconductor switch and the second semiconductor switch, N-type or P-type MOSFET switches 162 and 163 are illustrated; however, a semiconductor switch other than MOSFET switches such as a transistor or a thyristor may be used as the first semiconductor switch and the second semiconductor switch as long as the semiconductor switch is capable of switching operation.

Operations of Drug Solution Administration Apparatus

Operations of the drug solution administration apparatus will now be described with reference to the operation flowchart in FIG. 8.

First, the drug solution administration apparatus 100 that has been manufactured, for example, in a factory is stored under refrigeration in a factory and in a hospital. Then, when a medical worker is going to use the apparatus, the power switch 161 is turned on (S100). Since the power switch 161 is a momentary operation type push-button switch, the power switch is on only when being pressed. When the power switch 161 is turned on, power is supplied from the power supply unit 170 to the microcomputer 164 as shown in FIGS. 7 and 9, and the microcomputer 164 is started (S101). When the microcomputer 164 is started, the microcomputer 164 outputs an ON signal to the MOSFET switch 163 (S102). When the microcomputer 164 outputs the ON signal, the MOSFET switch 163 is turned on (S103). Assuming that the MOSFET switch 163 is, for example, a P-type transistor, the source terminal can be fixed to a potential (VDD) equal to or higher than a threshold voltage of the FET, and therefore, an ON signal output from the microcomputer 164 represents that a potential exceeding the threshold is applied from the microcomputer 164 to the gate terminal of the MOSFET switch 163.

Next, when the MOSFET switch 163 is turned on, the MOSFET switch 163 outputs an ON signal to the MOSFET switch 162. Assuming that the MOSFET switch 163 is, for example, a P-type transistor, the source potential is fixed to VDD, and therefore, an ON signal output from the MOSFET switch 163 represents that the VDD voltage is applied to the gate terminal of the MOSFET switch 162. Therefore, when the MOSFET switch 163 outputs the ON signal, the MOSFET switch 162 is turned on (S104). When the MOSFET switch 162 is turned on, the bypass circuit 166 bypassing the power switch 161 is formed as illustrated in FIG. 7 (S105). As a result, power is kept supplied from the power supply unit 170 to the microcomputer 164 even after the power switch 161 is turned off.

When power is supplied from the power supply unit 170 to the microcomputer 164, the microcomputer 164 reads and executes the drug solution administration program stored in the ROM to cause the pusher 130 (see FIGS. 5 and 6) to move little by little so that the drug solution is administered to the subject (S106). When the administration of the drug solution is finished, the microcomputer 164 ends the execution of the drug solution administration program (S107).

When the execution of the drug solution administration program is ended, the microcomputer 164 outputs an OFF signal to the MOSFET switch 163 (S108). Assuming that the MOSFET switch 163 is, for example, a P-type transistor, the source terminal is fixed to a potential (VDD) equal to or higher than a threshold voltage of the FET, and therefore, an OFF signal output from the microcomputer 164 represents that a potential lower than the threshold is applied from the microcomputer 164 to the gate terminal of the MOSFET switch 163. Upon receipt of the OFF signal, the MOSFET switch 163 is turned off (S109). Next, the MOSFET switch 162 is turned off as a result of the MOSFET switch 163 being turned off (S110). In this way, the MOSFET switch 163 cuts off a leakage current, which is indicated by an arrow in the figure and which would flow before power is applied from the protection circuit 165 disposed for protecting the microcomputer 164 from noise toward the power supply unit 170 if the MOSFET switch 163 were not provided. Specifically, as illustrated in FIG. 9, the MOSFET switch 163 cuts off a leakage current that would flow from the diode D1 in the protection circuit 165 toward the power supply unit 170 through the resistor R1 and the resistor R2.

As illustrated in FIGS. 10 and 11, in the case of a conventional power supply control circuit that does not include the MOSFET switch 163, a leakage circuit is formed from the diode D1, which forms the protection circuit 165 in the microcomputer 164, leading to the power supply unit 170 via the resistors R1 and R2. Although the leakage current is a very small current on the order of μA, the leakage current continuously flows while the drug solution administration apparatus 100 is stored under refrigeration, and thus the power of the power supply unit 170 formed of a button battery having a small electric capacity can be wastefully consumed. The power supply control circuit of the present embodiment illustrated in FIG. 9 helps prevent formation of a leakage circuit by providing the MOSFET switch 163. Note that the leakage current may be reduced by making a resistance value of R1+R2 extremely high, but practically the resistance value cannot be made extremely high because a very small current noise tends to be more influential when such resistance values are higher. Therefore, it is indispensable to provide the MOSFET switch 163. Therefore, in the case of the power supply control circuit in FIG. 9, the MOSFET switch 163 remains off during the time period when the MOSFET switch 162 is off before the power is turned on, that is, during the time period when the drug solution administration apparatus 100 is stored under refrigeration, thereby preventing formation of a leakage circuit. As a result, no leakage current flows, and thus the power of the power supply unit 170 is not wastefully consumed.

Thus, the power supply control circuit and the drug solution administration apparatus 100 including the power supply control circuit according to the present embodiment provides the cut-off circuit 167 to cut off a leakage circuit, thereby achieving power saving during storage. As a result, the electric capacity of the power supply unit 170 can be reduced, thereby achieving reduction in size and cost of the drug solution administration apparatus 100.

The power supply control circuit and the drug solution administration apparatus including the power supply control circuit according to the present disclosure have been described above by means of embodiments. However, the present disclosure is not limited to the individual configurations described above but can be modified as appropriate on the basis of descriptions in the claims.

For example, the power supply control circuit shown in FIG. 9 is not limited to the illustrated circuit configuration, and any other circuit configuration that can be conceived by those skilled in the art may be employed. In addition, the illustrated circuit configuration is an analog circuit configuration, but a digital circuit configuration may also be used.

The detailed description above describes embodiments of a power supply control circuit capable of achieving power saving and a drug solution administration apparatus including the power supply control circuit. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A power supply control circuit comprising:
a controller configured to control an operation of a control target;
a power supply unit configured to supply power to the controller;
a power switch configured to connect the power supply unit and the controller;
a bypass circuit that includes a first semiconductor switch and is capable of bypassing the power switch to maintain connection between the power supply unit and the controller;
a cut-off circuit that includes a second semiconductor switch and is disposed between the bypass circuit and the controller, the cut-off circuit including a signal supply source configured to supply a bypass circuit ON signal for turning on the first semiconductor switch;
wherein when the second semiconductor switch is in an off state, a leakage current generated between the controller and the power supply unit via the bypass circuit is cut off by the cut-off circuit;
when the second semiconductor switch is turned on by a switch-on signal output from the controller, the first semiconductor switch is turned on and the bypass circuit bypasses the power switch to maintain connection between the power supply unit and the controller;
the bypass circuit including an upstream circuit that branches from an upstream side of the power switch and is connected to an upstream side of the first semiconductor switch, a downstream circuit that is connected from a downstream side of the first semiconductor switch to a circuit between the power switch and the power supply unit, and a first input circuit for inputting the bypass circuit ON signal to the first semiconductor switch connected to a downstream side of the second semiconductor switch in the cut-off circuit; and
wherein the cut-off circuit includes the signal supply source that is connected to an upstream side of the second semiconductor switch, a second input circuit for inputting the switch-on signal from the controller to the second semiconductor switch, and a branch circuit that is branched from the second input circuit and is connected to a circuit between the signal supply source and the second semiconductor switch.

2. The power supply control circuit according to claim 1, wherein the signal supply source is a voltage supply circuit that supplies a voltage for turning on the first semiconductor switch.

3. The power supply control circuit according to claim 2, wherein the voltage supply circuit is a circuit branched from a circuit between a downstream side of the power supply unit and the controller.

4. The power supply control circuit according to claim 1, wherein the controller is a microcomputer that includes a program for controlling an operation of the control target.

5. The power supply control circuit according to claim 1, wherein the power switch is a momentary operation type push-button switch that is on only when being pressed.

6. The power supply control circuit according to claim 1, wherein the first semiconductor switch and the second semiconductor switch are N-type or P-type MOSFET switches.

7. A drug solution administration apparatus comprising: the power supply control circuit according to claim 1.

8. A drug solution administration system comprising:
a drug solution administration apparatus, the drug solution administration apparatus comprising:
a drug solution container configured to hold a drug solution;
a housing that holds the drug solution container;
a pusher configured to push the drug solution contained in the drug solution container;
a drive mechanism configured to move forward the pusher toward a distal end of the drug solution container; and
a detection part configured to sense a to-be-detected part of the pusher to detect completion of delivery of the drug solution on the basis of a sensing result; and
a controller configured to control operations of the drive mechanism to be controlled, the controller comprising:

a power supply unit configured to supply power to the controller;

a power switch configured to connect the power supply unit and the controller;

a bypass circuit that includes a first semiconductor switch and is capable of bypassing the power switch to maintain connection between the power supply unit and the controller;

a cut-off circuit that includes a second semiconductor switch and is disposed between the bypass circuit and the controller, the cut-off circuit including a signal supply source configured to supply a bypass circuit ON signal for turning on the first semiconductor switch;

wherein when the second semiconductor switch is in an off state, a leakage current generated between the controller and the power supply unit via the bypass circuit is cut off by the cut-off circuit;

when the second semiconductor switch is turned on by a switch-on signal output from the controller, the first semiconductor switch is turned on and the bypass circuit bypasses the power switch to maintain connection between the power supply unit and the controller;

the bypass circuit including an upstream circuit that branches from an upstream side of the power switch and is connected to an upstream side of the first semiconductor switch, a downstream circuit that is connected from a downstream side of the first semiconductor switch to a circuit between the power switch and the power supply unit, and a first input circuit for inputting the bypass circuit ON signal to the first semiconductor switch connected to a downstream side of the second semiconductor switch in the cut-off circuit; and wherein the cut-off circuit includes the signal supply source that is connected to an upstream side of the second semiconductor switch, a second input circuit for inputting the switch-on signal from the controller to the second semiconductor switch, and a branch circuit that is branched from the second input circuit and is connected to a circuit between the signal supply source and the second semiconductor switch.

9. The drug solution administration system according to claim 8, further comprising:

an administration instrument including a connector, a needle tube configured to puncture a living body, a cannula housing, a tube, and a puncture aid configured to assist in puncturing the living body with the needle tube.

10. The drug solution administration system according to claim 9, wherein the connector is configured to be connectable to the drug solution administration apparatus via an attachment that is fixed to the connector.

11. The drug solution administration system according to claim 10, further comprising:

a needle part configured to puncture a sealing member at the distal end of the drug solution container, and wherein the tube communicates with an inner cavity of the drug solution container via the needle part for connection; and wherein the drug solution is configured to be administered into a living body by being delivered to the puncture unit via the tube passing through a flow path formed inside the puncture unit and the needle tube.

12. A method of controlling power supply to a drug solution administration apparatus with a controller configured to control an operation of a control target, the method comprising:

supplying power to the controller from a power supply unit;

connecting the power supply unit and the controller with a power switch;

bypassing the power switch to maintain connection between the power supply unit and the controller with a bypass circuit that includes a first semiconductor switch;

disposing a cut-off circuit that includes a second semiconductor switch between the bypass circuit and the controller, the cut-off circuit including a signal supply source configured to supply a bypass circuit ON signal for turning on the first semiconductor switch;

wherein when the second semiconductor switch is in an off state, generating a leakage current between the controller and the power supply unit via the bypass circuit is cut off by the cut-off circuit;

when the second semiconductor switch is turned on by a switch-on signal output from the controller, turning on the first semiconductor switch and bypassing the power switch with the bypass circuit to maintain connection between the power supply unit and the controller;

supplying a bypass circuit ON signal for turning on the first semiconductor switch with a signal supply source in the cut-off circuit;

connecting an upstream circuit that branches from an upstream side of the power switch to an upstream side of the first semiconductor switch;

connecting a downstream circuit from a downstream side of the first semiconductor switch to a circuit between the power switch and the power supply unit;

inputting the b pass circuit ON signal to the first semiconductor switch connected to a downstream side of the second semiconductor switch in the cut-off circuit with a first input circuit;

connecting the signal supply source to an upstream side of the second semiconductor switch;

inputting the switch-on signal from the controller to the second semiconductor switch with a second input circuit; and connecting a branch circuit that is branched from the second input circuit to a circuit between the signal supply source and the second semiconductor switch.

13. The method according to claim 12, further comprising:

supplying a voltage for turning on the first semiconductor switch with a voltage supply circuit.

14. The method according to claim 13, wherein the voltage supply circuit is a circuit branched from a circuit between a downstream side of the power supply unit and the controller.

15. The method according to claim 12, wherein the controller is a microcomputer that includes a program for controlling an operation of the control target.

16. The method according to claim 12, wherein the power switch is a momentary operation type push-button switch that is on only when being pressed, and the first semiconductor switch and the second semiconductor switch are N-type or P-type MOSFET switches.

* * * * *